United States Patent
Hayakawa et al.

(10) Patent No.: US 11,751,876 B2
(45) Date of Patent: Sep. 12, 2023

(54) APPARATUSES FOR ANASTOMOSIS OF TUBULAR VESSELS AND RELATED METHODS

(71) Applicant: EasyfloMicro Inc., Winnipeg (CA)

(72) Inventors: Thomas Edward Jo Hayakawa, Winnipeg (CA); Daniel William Rickey, Winnipeg (CA)

(73) Assignee: EasyfloMicro Inc., Winnipeg (CA)

( * ) Notice: Subject to any disclaimer, the term of this patent is extended or adjusted under 35 U.S.C. 154(b) by 0 days.

(21) Appl. No.: 17/748,968

(22) Filed: May 19, 2022

(65) Prior Publication Data

US 2022/0273311 A1 Sep. 1, 2022

Related U.S. Application Data

(63) Continuation of application No. 17/291,554, filed as application No. PCT/IB2020/000358 on May 5, 2020.

(60) Provisional application No. 62/844,396, filed on May 7, 2019.

(51) Int. Cl.
*A61B 17/11* (2006.01)

(52) U.S. Cl.
CPC ....... *A61B 17/11* (2013.01); *A61B 2017/1107* (2013.01); *A61B 2017/1132* (2013.01)

(58) Field of Classification Search
CPC .... A61B 2017/1107; A61B 2017/1132; A61B 2017/11
See application file for complete search history.

(56) References Cited

U.S. PATENT DOCUMENTS

| | | | |
|---|---|---|---|
| 1,151,300 A | 8/1915 | Soresi |
| 1,470,707 A | 10/1923 | Bates |
| 2,428,918 A | 10/1947 | Miller |
| 2,453,056 A | 11/1948 | Edwin |
| 2,638,901 A | 5/1953 | Sugarbaker |
| 3,155,095 A | 11/1964 | Brown |
| 3,191,842 A | 6/1965 | Fischer et al. |
| 3,221,746 A | 12/1965 | Noble |
| 3,254,650 A | 6/1966 | Collito |

(Continued)

FOREIGN PATENT DOCUMENTS

| KR | 101151770 B1 | 5/2012 |
|---|---|---|
| WO | 2014200224 A1 | 12/2014 |

OTHER PUBLICATIONS

Written Opinion for International Application No. PCT/IB2020/000358, dated Sep. 11, 2020, 12 pages.

*Primary Examiner* — Diane D Yabut
*Assistant Examiner* — Christina C Lauer
(74) *Attorney, Agent, or Firm* — Lewis Roca Rothgerber Christie LLP

(57) ABSTRACT

An apparatus for anastomosis of tubular structures includes two annular bodies. Each annular body has a first side, a second side, a central axis extending between the first and second sides, an inner wall defining a passageway that is open to the first and second sides for passing a tubular structure therethrough, and a plurality of spikes each extending from a base connected to the second side of the annular body to a pointed free end configured to pierce the tubular structure. The spikes are angled relative to the central axis such that for each of the spikes, the free end is positioned farther from the central axis in a radial direction than the base is to the central axis.

18 Claims, 6 Drawing Sheets

(56) References Cited

U.S. PATENT DOCUMENTS

| | | | |
|---|---|---|---|
| 3,254,651 | A | 6/1966 | Collito |
| 3,258,012 | A | 6/1966 | Nakayama et al. |
| 3,265,069 | A | 8/1966 | Healey, Jr. et al. |
| 3,316,914 | A | 5/1967 | Collito |
| 3,357,432 | A | 12/1967 | Sparks |
| 3,496,939 | A | 2/1970 | Odiaga et al. |
| 3,683,926 | A | 8/1972 | Suzuki |
| 3,771,526 | A | 11/1973 | Rudie |
| 3,774,615 | A | 11/1973 | Lim et al. |
| 3,790,057 | A | 12/1974 | Razgulov et al. |
| 3,908,662 | A | 9/1975 | Razgulov et al. |
| 3,974,835 | A | 8/1976 | Hardy, Jr. |
| 3,981,051 | A | 9/1976 | Brumlik |
| 4,055,186 | A | 10/1977 | Leveen |
| 4,076,162 | A | 2/1978 | Kapitavov et al. |
| 4,214,586 | A | 7/1980 | Mericle |
| 4,214,587 | A | 7/1980 | Sakura, Jr. |
| 4,233,981 | A | 11/1980 | Schomacher |
| 4,267,842 | A | 5/1981 | Archibald |
| 4,294,255 | A | 10/1981 | Geroc |
| 4,350,160 | A | 9/1982 | Kolesov et al. |
| 4,470,415 | A | 9/1984 | Wozniak |
| 4,474,181 | A | 10/1984 | Schenck |
| 4,523,592 | A | 6/1985 | Daniel |
| 4,553,542 | A | 11/1985 | Schenck et al. |
| 4,593,693 | A | 6/1986 | Schenck |
| 4,607,637 | A | 8/1986 | Berggren et al. |
| 4,624,255 | A | 11/1986 | Schenck et al. |
| 4,624,257 | A | 11/1986 | Berggren et al. |
| 4,657,019 | A | 4/1987 | Walsh et al. |
| 4,665,917 | A | 5/1987 | Clanton et al. |
| 4,693,249 | A | 9/1987 | Schenck et al. |
| 4,747,407 | A | 5/1988 | Liu et al. |
| 4,771,775 | A | 9/1988 | Walsh et al. |
| 4,787,386 | A | 11/1988 | Walsh et al. |
| 4,873,975 | A | 10/1989 | Walsh et al. |
| 4,873,976 | A | 10/1989 | Schreiber |
| 4,917,087 | A | 4/1990 | Walsh et al. |
| 4,917,090 | A | 4/1990 | Berggren et al. |
| 4,917,091 | A | 4/1990 | Berggren et al. |
| 4,929,240 | A | 5/1990 | Kirsch et al. |
| 4,930,502 | A | 6/1990 | Chen |
| 4,997,439 | A | 3/1991 | Chen |
| 5,089,008 | A | 2/1992 | Chen |
| 5,123,908 | A | 6/1992 | Chen |
| 5,180,392 | A | 1/1993 | Skeie et al. |
| 5,188,638 | A | 2/1993 | Tzakis |
| 5,250,057 | A * | 10/1993 | Chen ............... A61B 17/11 606/154 |
| 5,250,058 | A | 10/1993 | Miller et al. |
| 5,254,127 | A | 10/1993 | Wholey et al. |
| 5,314,436 | A | 5/1994 | Wilk |
| 5,336,233 | A * | 8/1994 | Chen ............... A61B 17/11 606/154 |
| 5,486,187 | A | 1/1996 | Schenck |
| 5,503,635 | A | 4/1996 | Sauer et al. |
| 5,549,122 | A | 8/1996 | Detweilwer |
| 5,562,690 | A | 10/1996 | Green et al. |
| 5,653,744 | A | 8/1997 | Khouri |
| 5,695,504 | A | 12/1997 | Gifford, III et al. |
| 5,697,943 | A | 12/1997 | Sauer et al. |
| 5,817,113 | A | 10/1998 | Gifford, III et al. |
| 6,017,352 | A | 1/2000 | Nash et al. |
| 6,030,395 | A * | 2/2000 | Nash ............... A61B 17/11 606/153 |
| 6,036,704 | A | 3/2000 | Yoon |
| 6,110,188 | A | 8/2000 | Narciso, Jr. |
| 6,171,321 | B1 | 1/2001 | Gifford, III et al. |
| 6,241,741 | B1 | 6/2001 | Duhaylongsod et al. |
| 6,248,117 | B1 | 6/2001 | Blatter |
| 6,254,618 | B1 | 7/2001 | Dakov |
| 6,280,460 | B1 | 8/2001 | Bolduc et al. |
| 6,491,704 | B2 | 12/2002 | Gifford, III et al. |
| 6,491,705 | B2 | 12/2002 | Gifford, III et al. |
| 6,494,889 | B1 | 12/2002 | Fleischman et al. |
| 6,503,258 | B1 | 1/2003 | Filho |
| 6,537,288 | B2 | 3/2003 | Vargas et al. |
| 6,565,581 | B1 | 5/2003 | Spence et al. |
| 6,569,173 | B1 | 5/2003 | Blatter et al. |
| 6,629,988 | B2 | 10/2003 | Weadock |
| 6,666,873 | B1 | 12/2003 | Cassell |
| 6,676,678 | B2 | 1/2004 | Gifford, III et al. |
| 6,699,245 | B2 | 3/2004 | Dinger et al. |
| 6,730,103 | B2 | 5/2004 | Dakov |
| 6,736,825 | B2 | 5/2004 | Blatter et al. |
| 6,746,456 | B2 | 6/2004 | Xiao |
| 6,776,785 | B1 | 8/2004 | Yencho et al. |
| 6,802,847 | B1 | 10/2004 | Carson et al. |
| 6,811,555 | B1 | 11/2004 | Willis et al. |
| 6,890,338 | B1 | 5/2005 | Davis et al. |
| 6,896,687 | B2 | 5/2005 | Dakov |
| 6,899,718 | B2 | 5/2005 | Gifford, III et al. |
| 6,905,504 | B1 | 6/2005 | Vargas |
| 6,942,675 | B1 | 9/2005 | Vargas |
| 6,962,595 | B1 | 11/2005 | Chamness et al. |
| 6,962,596 | B2 | 11/2005 | Bolduc et al. |
| 6,984,238 | B2 | 1/2006 | Gifford, III et al. |
| 6,994,714 | B2 | 2/2006 | Vargas et al. |
| 7,029,482 | B1 | 4/2006 | Vargas et al. |
| 7,063,712 | B2 | 6/2006 | Vargas et al. |
| 7,112,211 | B2 | 9/2006 | Gifford et al. |
| 7,182,771 | B1 | 2/2007 | Houser et al. |
| 7,192,400 | B2 | 3/2007 | Campbell et al. |
| 7,347,864 | B2 | 3/2008 | Vargas |
| 7,585,306 | B2 | 9/2009 | Abbott et al. |
| 7,651,510 | B2 | 1/2010 | Bolduc et al. |
| 7,691,140 | B2 | 4/2010 | Bates et al. |
| 7,749,239 | B2 | 7/2010 | De Winter |
| 7,922,734 | B2 | 4/2011 | Blatter et al. |
| 8,066,723 | B2 | 11/2011 | Suyker et al. |
| 8,109,949 | B2 | 2/2012 | Blatter et al. |
| 8,162,963 | B2 | 4/2012 | Abbott |
| 8,182,498 | B2 | 5/2012 | Suyker et al. |
| 8,313,013 | B2 | 11/2012 | Kuester, III et al. |
| 8,361,092 | B1 | 1/2013 | Asfora |
| 8,574,246 | B1 | 11/2013 | Bender et al. |
| 8,603,114 | B2 | 12/2013 | Kim et al. |
| 8,617,191 | B2 | 12/2013 | Lui |
| 8,701,963 | B2 | 4/2014 | Bach et al. |
| 8,795,300 | B2 | 8/2014 | Bilotti et al. |
| 8,858,579 | B2 | 10/2014 | Suyker et al. |
| 9,642,623 | B2 | 5/2017 | Agarwal et al. |
| 9,675,357 | B2 | 6/2017 | Suyker et al. |
| 2001/0001826 | A1 | 5/2001 | Bolduc et al. |
| 2001/0039425 | A1 | 11/2001 | Dakov |
| 2003/0014064 | A1 | 1/2003 | Blatter |
| 2003/0055441 | A1 | 3/2003 | Suyker et al. |
| 2003/0130671 | A1 | 7/2003 | DuhaylongSOd et al. |
| 2004/0068278 | A1 | 4/2004 | Fleischman et al. |
| 2004/0181244 | A1 | 9/2004 | Lee |
| 2004/0186489 | A1 | 9/2004 | Lee |
| 2004/0225306 | A1 | 11/2004 | Blatter et al. |
| 2004/0230209 | A1 | 11/2004 | Masroor |
| 2005/0021060 | A1 | 1/2005 | Davis et al. |
| 2005/0027308 | A1 | 2/2005 | Davis et al. |
| 2005/0033329 | A1 | 2/2005 | Bombard et al. |
| 2005/0033330 | A1 | 2/2005 | Vargas et al. |
| 2005/0038456 | A1 | 2/2005 | Vargas et al. |
| 2005/0075657 | A1 | 4/2005 | Bombard et al. |
| 2005/0143758 | A1 | 6/2005 | Abbott et al. |
| 2005/0149071 | A1 | 7/2005 | Abbott et al. |
| 2005/0154406 | A1 | 7/2005 | Bombard et al. |
| 2005/0182430 | A1 | 8/2005 | Schenck |
| 2005/0209614 | A1 | 9/2005 | Fenter et al. |
| 2005/0234483 | A1 | 10/2005 | Yencho et al. |
| 2006/0142791 | A1 | 6/2006 | Chapman |
| 2007/0239180 | A1 | 10/2007 | Kuester, III et al. |
| 2007/0250082 | A1* | 10/2007 | Kansoul ............. A61B 17/11 606/153 |
| 2008/0269784 | A1 | 10/2008 | Abbott et al. |
| 2009/0012543 | A1 | 1/2009 | Kansoul |
| 2010/0063520 | A1 | 3/2010 | Bilotti |
| 2010/0114301 | A1* | 5/2010 | Heaton, II ............. A61B 50/30 623/1.36 |

(56) References Cited

U.S. PATENT DOCUMENTS

| | | |
|---|---|---|
| 2011/0106119 A1 | 5/2011 | Lin et al. |
| 2011/0230902 A1 | 9/2011 | Kansoul |
| 2011/0319916 A1 | 12/2011 | Kim et al. |
| 2012/0123451 A1 | 5/2012 | Asfora et al. |
| 2013/0204275 A1 | 8/2013 | Agarwal et al. |
| 2014/0364882 A1 | 12/2014 | Tulleken et al. |
| 2015/0088172 A1 | 3/2015 | Watanabe |
| 2015/0230798 A1 | 8/2015 | Gronlund |
| 2016/0206316 A1 | 7/2016 | Johnson et al. |
| 2017/0128072 A1 | 5/2017 | Wang et al. |

* cited by examiner

APPARATUSES FOR ANASTOMOSIS OF TUBULAR VESSELS AND RELATED METHODS

CROSS-REFERENCE TO RELATED APPLICATION(S)

This application is a continuation of U.S. patent application Ser. No. 17/291,554, filed May 5, 2021, which is a National Phase Patent Application and claims priority to and the benefit of International Application No. PCT/IB2020/000358, filed on May 5, 2020, which claims priority to and the benefit of U.S. Provisional Patent Application No. 62/844,396, filed May 7, 2019, the contents of which are hereby incorporated by reference in their entirety.

BACKGROUND

Field

Embodiments of the present disclosure relate to devices or apparatuses for connecting tubular vessels or other tubular structures, and related methods of use. In particular, the devices and methods can be used for anastomoses of tubular vessels in various medical procedures. Generally speaking, such devices are typically permanently implantable in the human body and are particularly suited for performing vascular anastomoses for connecting two ends of an artery or two separate arteries.

Description of Related Art

An anastomosis is performed to functionally connect ends of a tubular vessel or structure or of two separate tubular vessels or structures. More specifically, circulatory anastomoses are performed on blood vessels. Typically in microsurgery, a circulatory anastomosis is performed either by hand, for example, via application of nylon microsurgery sutures at the connection site, or with a permanently implantable mechanical apparatus or device at the connection site. Although a permanently implantable mechanical arrangement for performing a circulatory anastomosis on small vessels (e.g., 1 mm to 4 mm diameter) is generally rather common now, such mechanical devices are typically used only for anastomosis of veins. One of the devices most commonly used in the medical field is a coupler described in U.S. Pat. No. 4,917,090 to Berggren et al., which discloses a small annulus or ring with a series of straight spikes to which walls of veins are fastened. The straight spikes of the Berggren arrangement are oriented at 90 degrees to a surface of the annulus, which receives a wall of a vein in an everted condition, and thus the spikes are also oriented at 90 degrees to the everted wall of the vein. The spikes are mounted to the annulus of the Berggren arrangement in a ring shape, and the annulus is compressed together and coupled with another like annulus. The spikes which act to hold the vein to the coupler ring also act to interconnect the coupler ring with the other or opposite coupler ring to thereby hold the two ends of the vein or veins together.

Veins have thin flexible walls and are easily everted, pulled over, and then anchored on to the spikes of mechanical coupling devices such as the Berggren arrangement. As such, the successful use of this coupler design has been reported extensively for anastomosis of veins. However, this coupler design is not well suited for use with arteries, because in contrast to veins, arteries often have thick non-compliant walls that are more difficult to evert over the Berggren coupler's spikes without such eversion leading to failures such as a fissure in the arteries, fracture of the arteries, and/or disruption of the inner lining of the arterial vessel wall that often leads to clotting, thrombosis, and failure. Additionally, arterial pressures are much higher than venous pressures, and therefore a successful anastomosis between arteries will generally require a stronger and more robust connection than an anastomosis between veins. Therefore, among other deficiencies for application to arterio-arterial anastomoses, properties of the Berggren coupler, such as the orientation of the spikes at 90 degrees to the surface that receives the everted vessel wall, may not be well-suited to arterial application.

Additionally, in the Berggren arrangement, both mating rings are always identical, but may still be used for the anastomosis of different diameter veins, even if the internal passageway is oversized relative to one or both of the veins, because the general compliance of veins allows stretching of smaller diameter veins for expansion to fit on a larger size coupler. This stretching and expansion cannot be accomplished with thick walled arteries, in order to suit a coupler ring which is too large relative to the artery.

Consequently, this known coupler design is not well suited for many applications, including arterial anastomoses, and are therefore rarely used for such applications. In other words, while devices have already been successfully developed for the anastomosis of veins, it is universally accepted that the current widely used devices used for anastomosing veins can very rarely be used successfully for arteries. Consequently, alternatively to using a coupler, arteries are typically still sutured together by hand by a surgeon, using for example, nylon microsurgery sutures, which is a slow and lengthy process requiring a large amount of skill.

SUMMARY

Therefore, there is a need for an improved mechanical implant or other medical device that can be used for anastomosing arteries. Hence, it is an object of embodiments of the present disclosure to provide an improved coupling assembly that facilitates anastomoses of arteries in a quicker and more effective manner and that is easy for practitioners to adopt, without occurrence of various potential failures that may result from arterio-arterial anastomoses.

According to an aspect of some embodiments, there is provided an apparatus for anastomosis of tubular vessels including a pair of annular bodies, each annular body extending along an axis of the body from a first side of the body to a second side thereof. Each annular body defines a passageway which opens at the first side and at the second side and is arranged for passing a free end of one of the vessels therethrough from the first side to the second side. The second sides of the annular bodies are arranged to receive the free ends of the vessels in an everted condition suited for anastomosis. Each annular body has a plurality of spikes at the second side thereof, the spikes having pointed tips for piercing the free end of said one of the vessels in the everted condition, such that the respective vessel is coupled to the annular body in the everted condition. The spikes on each annular body are arranged at radially spaced locations from the passageway and at angularly spaced locations from one another relative to the axis of the body. Each of the spikes on the respective annular body projects axially and radially outwardly from the second side so as to retain the pierced tubular vessel in the everted condition.

In one arrangement, the passageway is flared in a direction oriented from the first side of the body towards the second side thereof, such that an inner peripheral surface delimiting the passageway diverges from the axis of the body in said direction so that the free end of each vessel can be arranged in the everted condition at the second side of the body, for example, without rupturing.

According to another aspect of some embodiments, there is provided an apparatus for anastomosis of tubular vessels including a pair of annular bodies, each annular body extending along an axis of the body from a first side of the body to a second side thereof. Each annular body has an inner peripheral surface delimiting a passageway which opens at the first side and at the second side and is arranged for passing a free end of one of the vessels therethrough from the first side to the second side. The second sides of the annular bodies are arranged to receive the free ends of the vessels in an everted condition suited for anastomosis. Each annular body has a plurality of spikes at the second side thereof, the spikes having pointed tips for piercing the free end of said one of the vessels in the everted condition, such that the respective vessel is coupled to the annular body in the everted condition. The spikes on each annular body are arranged at radially spaced locations from the passageway and at angularly spaced locations from one another relative to the axis of the body. The passageway is flared in a direction oriented from the first side of the body towards the second side thereof, such that the inner peripheral surface diverges from the axis of the body in said direction so that the free end of each vessel can be arranged in the everted condition at the second side of the body, for example, without rupturing.

In one arrangement, the passageways of the annular bodies have different diameters, but the annular bodies have substantially common outer diameters measured at outer peripheries of the annular bodies, to anastomose the vessels having different diameters.

According to yet another aspect of some embodiments, there is provided an apparatus for anastomosis of tubular vessels including a pair of annular bodies, each annular body extending along an axis of the body from a first side of the body to a second side thereof. Each annular body defines a passageway which opens at the first side and at the second side and is arranged for passing a free end of one of the vessels therethrough from the first side to the second side. The second sides of the annular bodies are arranged to receive the free ends of the vessels in an everted condition suited for anastomosis. Each annular body has a plurality of spikes at the second side thereof, the spikes having pointed tips for piercing the free end of said one of the vessels in the everted condition, such that the respective vessel is coupled to the annular body in the everted condition. The spikes on each annular body are arranged at radially spaced locations from the passageway and at angularly spaced locations from one another relative to the axis of the body. The passageways of the annular bodies have different diameters, but the annular bodies have substantially common outer diameters measured at outer peripheries of the annular bodies, to anastomose the vessels having different diameters.

In some embodiments, each of the spikes on the respective annular body project axially and radially outwardly from the second side so as to retain the pierced tubular vessel in the everted condition.

In one arrangement, the passageway is flared in a direction oriented from the first side of the body towards the second side thereof, such that an inner peripheral surface delimiting the passageway diverges from the axis of the body in said direction so that the free end of each vessel can be arranged in the everted condition at the second side of the body, for example, without rupturing.

In some embodiments, the apparatus further includes a plurality of coupler pins on at least one of the annular bodies and projecting from the second side thereof, the coupler pins being distinct from the spikes, for connecting the annular bodies to one another in a coupled condition in which the vessels are anastomosed.

In some embodiments, the coupler pins are arranged at locations on said at least one of the annular bodies which are spaced radially outwardly from the spikes, for example, so as not to pierce the free end of the respective tubular vessel in the everted condition.

In some embodiments, each annular body includes an inner peripheral surface delimiting the passageway and extending from the first side to the second side, an annular end surface at the second side which extends radially outwardly from the inner peripheral surface to an outer periphery of the respective annular body, and a plurality of receptacles defined in the end surface and located in axial alignment with the spikes on the other one of the annular bodies so as to receive said spikes in a coupled condition in which the vessels are anastomosed, each receptacle being sized in a radial direction larger than a diameter of a respective one of said spikes so as to receive the respective spike in the coupled condition without deflecting the respective spike.

In some embodiments, each annular body includes a plurality of receptacles formed in the second side for receiving the spikes on the other one of the annular bodies in a coupled condition in which the vessels are anastomosed, and each annular body further includes an indexing surface at an outer periphery of the body for aligning the receptacles and the spikes angularly relative to the axes of the bodies.

In some embodiments, the spikes projecting from the second side of the respective annular body are supported at the end surface thereof.

In some embodiments, where the passageways of the annular bodies have the different diameters and where the spikes on each annular body are supported on the end surface at the second side thereof, the spikes which are on the annular body having a larger one of the different diameters of the passageways are supported on the end surface thereof at locations spaced further in a radial direction from the axis of the annular body than the spikes which are on the annular body having a smaller one of the different diameters of the passageways in relation to the axis thereof.

In one arrangement, the spikes on the annular bodies are located at substantially common radial distances from where the end surfaces of the annular bodies meet the inner peripheral surfaces thereof. In other words, regardless of the size of the passageway of each annular body, a radial distance between an edge of the passageway and each of the spikes remains substantially constant. In this manner, an annular body that has a larger passageway will have spikes that are located farther from the central axis in a radial direction than the spikes on an annular body that has a smaller passageway. In some embodiments, the receptacles of these annular bodies may all have similar positioning and orientation on different annular bodies, such that the similarly arranged receptacles can receive spikes located at different radial positions on different annular bodies. Meanwhile, the lengths or other size characteristics of the receptacles on different annular bodies can be slightly different due to the size of the corresponding passageway, so long as the receptacles are sufficiently sized to receive the spikes on the various other annular bodies with which a particular annular body is configured to be used.

In some embodiments, where each of the spikes on the respective annular body projects axially and radially outwardly from the second side thereof so as to retain the pierced tubular vessel in the everted condition and where each annular body further includes the receptacles defined in the end surface thereof for receiving the spikes of the other one of the annular bodies in a coupled condition in which the vessels are anastomosed, the receptacles of the annular body are located generally in axial alignment with the spikes on the other one of the annular bodies and each receptacle is sized in a radial direction larger than a diameter of a respective one of the spikes on the other one of the annular bodies so as to receive the respective spike in the coupled condition without deflecting the respective spike, and further the receptacles of the annular bodies are sized substantially the same in the radial direction and are located at substantially common radial distances from the outer peripheries of the annular bodies.

In some embodiments, the spikes on the annular bodies are each inclined at substantially common angles relative to the axis of the respective one of the annular bodies on which the spike is located.

In some embodiments, where each annular body includes the coupler pins projecting from the second side thereof, which are distinct from the spikes, and arranged at locations which are spaced radially outwardly from the spikes for connecting the annular bodies in the coupled condition, for example, without piercing the free end of the respective tubular vessel in the everted condition and where the coupler pins and the spikes projecting from the second side of the respective annular body are supported at the end surface thereof, the coupler pins on the annular bodies can, but may not necessarily be, spaced from the axis of the respective annular body and/or the outer peripheries thereof at common radial distances.

In some embodiments, the passageway of each annular body is flared in a direction oriented from the first side of the body towards the second side thereof such that an inner peripheral surface delimiting the passageway diverges, for example, in a flat or curved manner, from the axis of the body in said direction so that the free end of each vessel can be arranged in the everted condition at the second side of the body, for example, without rupturing, the inner peripheral surfaces of the annular bodies each diverging at substantially the same angle relative to the axis of the respective one of the annular bodies.

According to yet another aspect of some embodiments, there is provided a method of anastomosing tubular vessels including providing two annular bodies each defining a passageway from a first side of the body to a second side thereof, for each vessel, passing a free end of the vessel through the passageway of a respective one of the bodies so as to locate said free end at the second side thereof, for each vessel, attaching the free end thereof in an everted condition to a ring of spikes which are projecting from the second side of the respective body in diverging condition relative to the passageway, and after the free ends of the vessels are attached at the second sides of the annular bodies, coupling the annular bodies so as to anastomose the vessels.

BRIEF DESCRIPTION OF THE DRAWINGS

Further features and advantages of embodiments of the present disclosure will now be described in conjunction with exemplary embodiments as illustrated in the accompanying drawings, in which.

DETAILED DESCRIPTION

Figure 1:
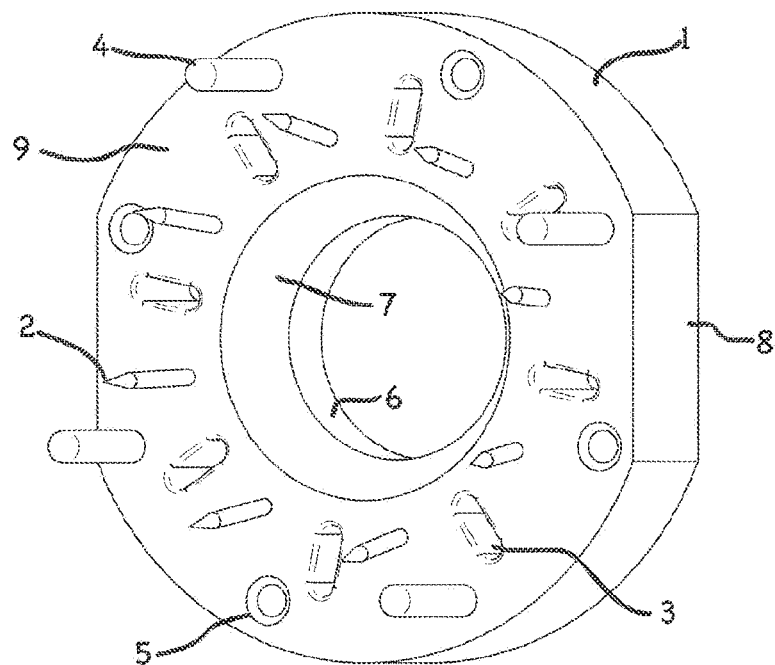
FIG. 1 shows an oblique perspective view of one coupler ring of a coupling device or apparatus according to an embodiment of the present disclosure.

The accompanying figures show various apparatuses according to embodiments of the present disclosure that can be used for anastomosis of tubular vessels, and that is particularly suited for, but not necessarily limited to, anastomosing arteries.

FIGS. 1-7 show various views of a coupling assembly configured, for example, for anastomosing arteries according to an embodiment of the present disclosure. In some embodiments, the coupling assembly includes a pair of annuli 1 or generally ring-shaped structures that are configured to be joined together to form the coupling assembly. The annuli 1 shown in FIGS. 1-7 are generally circular in shape, but other embodiments of the coupling device may include annuli that are formed in various different shapes and sizes, based on the particular application of the device. In some embodiments, the pair of annuli may have identical structures for ease of manufacture and use.

Each annulus 1 generally has a first side 12 and a second side 11, and a central axis A that extends between the sides 11, 12. The sides 11, 12 may both be generally planar and may extend substantially parallel with one another. An outer surface of the annulus 1 is formed between the sides 11, 12, and extends circumferentially around the central axis A. A central bore or aperture 6 is formed through the annulus 1 and extends coaxially with the central axis A. The annulus 1 may have a relatively thin height or thickness measured in a direction of the central axis A, and for example, when compared to the width of the annulus 1 measured in a direction perpendicular to the central axis A. Each annulus 1 is typically manufactured from one or more of various biocompatible materials, and in an exemplary embodiment, of one or more hard biocompatible materials.

The annuli 1 of the coupling assembly are configured to be coupled to one another in an orientation where the second sides 11 of the annuli 1 face one another. The second side 11 of each annulus 1 has a generally planar face 9 that extends radially between the outer surface of the annulus 1 and the aperture 6, and on which various different features of the coupling assembly are formed. First, on each opposed face 9 are a plurality of projections or spikes 2. The spikes 2 may be situated circumferentially around the central axis A, and may be for example, arranged at a same radial distance from the central axis A as one another, and/or equally spaced apart from one another around the face 9. In the embodiment shown in FIGS. 1-7, there are a total of eight spikes 2 formed on each face 9, equidistantly spaced apart 45 degrees from one another relative to the central axis A. In other embodiments, more or less than eight spikes 2 may be formed on each annulus 1, depending on each application and characteristics of each particular procedure. For example, an annulus with an appropriate number of spikes may be selected which the practitioner feels is necessary to adequately maintain a connection between the annulus and a connected tubular structure that is being anastomosed with the annulus, without damaging the tubular structure. In exemplary embodiments, each of the spikes 2 is angled or tilted away from the central axis A such that a free end of each spike 2 is positioned farther away from the central axis A than a base of each spike 2 that is connected to the face 9. The orientation of the angulation may be along radial directions relative to the central axis A, or in other directions in alternative embodiments. In the embodiment shown in FIGS. 1-7, the spikes 2 are angled by about 10 degrees relative to the central axis A, as illustrated and best seen, for example, in FIG. 7 (e.g., an interior angle formed between the spikes 2 and the central axis A is about 10 degrees). However, an angulation of each of the spikes in other embodiments may be more or less than about 10 degrees, depending on the properties of each procedure, so long as the free ends of the spikes are angled outwards as described, and do not extend parallel to the central axis A. In this manner, an arterial wall may remain more securely attached to a connected annulus 1. The spikes 2 are pointed on their free ends, for example, to facilitate easier puncturing through or otherwise attaching to a tubular structure connected thereto. Furthermore, the spikes 2 may be made from stainless steel or one of or a combination of any other similar biocompatible materials. The spikes 2 may each have an exposed length and diameter that is selected to be appropriate to the diameter of an artery or other tubular structure to be attached thereto. For example, for an anastomosis of an approximately 3 mm artery, an annulus 1 may be selected with spikes 2 each having a length of about 2 mm and a diameter of about 0.2 mm. Other spike lengths and diameters may be appropriate for other applications. In some embodiments, spikes 2 may also include other surface features, for example, a roughened finish, to even more securely attach to an arterial wall and prevent sliding off. Also as best seen in the cross-section of FIG. 7, the spikes 2 are formed separately from the annuli 1, and are embedded into or otherwise affixed to its corresponding annulus 1. In other embodiments, the spikes may be monolithic with or otherwise integrally formed with their respective annuli.

Alternating with the spikes 2 on each face 9 are receptacles 3, that are formed, for example, as slots or holes, each of which is sized and positioned for receiving and accommodating a corresponding one of the spikes 2 that is mounted on an opposite annulus 1 when the coupling device is assembled together. Generally, there are a same number of receptacles 3 as there are spikes 2. For example, in the embodiment in FIGS. 1-7 that has eight spikes 2, there are eight corresponding receptacles 3, where the spikes 2 and receptacles 3 are alternately arranged circumferentially around the aperture 6. In this manner, when the faces 9 of two annuli 1 are aligned and assembled together, the spikes 2 from one annulus 1 can be aligned with the receptacles 3 of the opposite annulus 1, and vice versa, such that opposing spikes 2 can be alternately received in corresponding receptacles 3, and the annuli 1 can thereby be pressed closer together towards one another. In the embodiment shown, the receptacles 3 each has an elongate profile, with a long axis aligned in a radial direction relative to the central axis A. The receptacles 3 are also constructed larger than the spikes 2, such that when two annuli 1 are advanced towards one another coaxially, the receptacles 3 are large enough and oriented to allow the spikes 2 to advance therein without significantly angulating or otherwise manipulating the annuli 1 relative to one another. Other spike and receptacle sizes and shapes are also acceptable, so long as the receptacles are configured to permit advancement of the corresponding angled spikes therein when a pair of annuli 1 are coaxially advanced towards one another.

Figure 4:
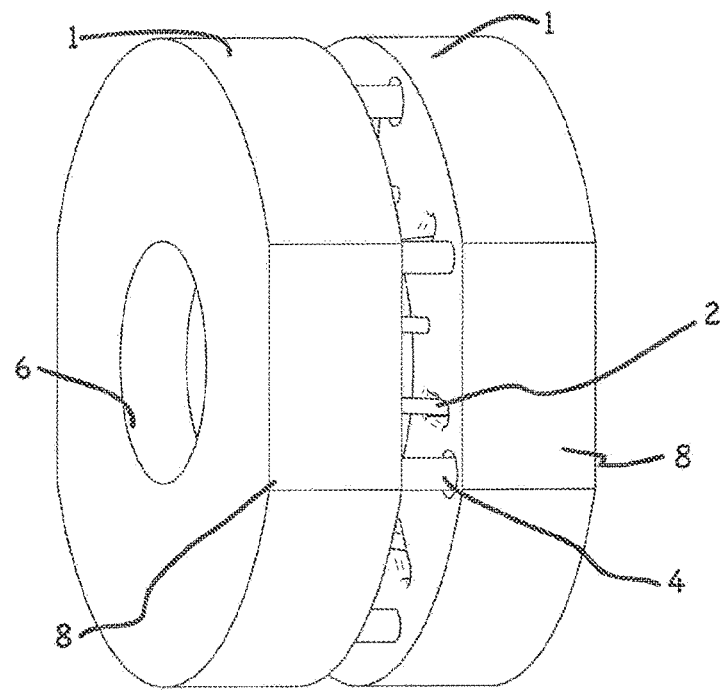
FIG. 4 shows a perspective side view of a pair of coupler rings joined together to form the assembled coupling device.
Figure 5:
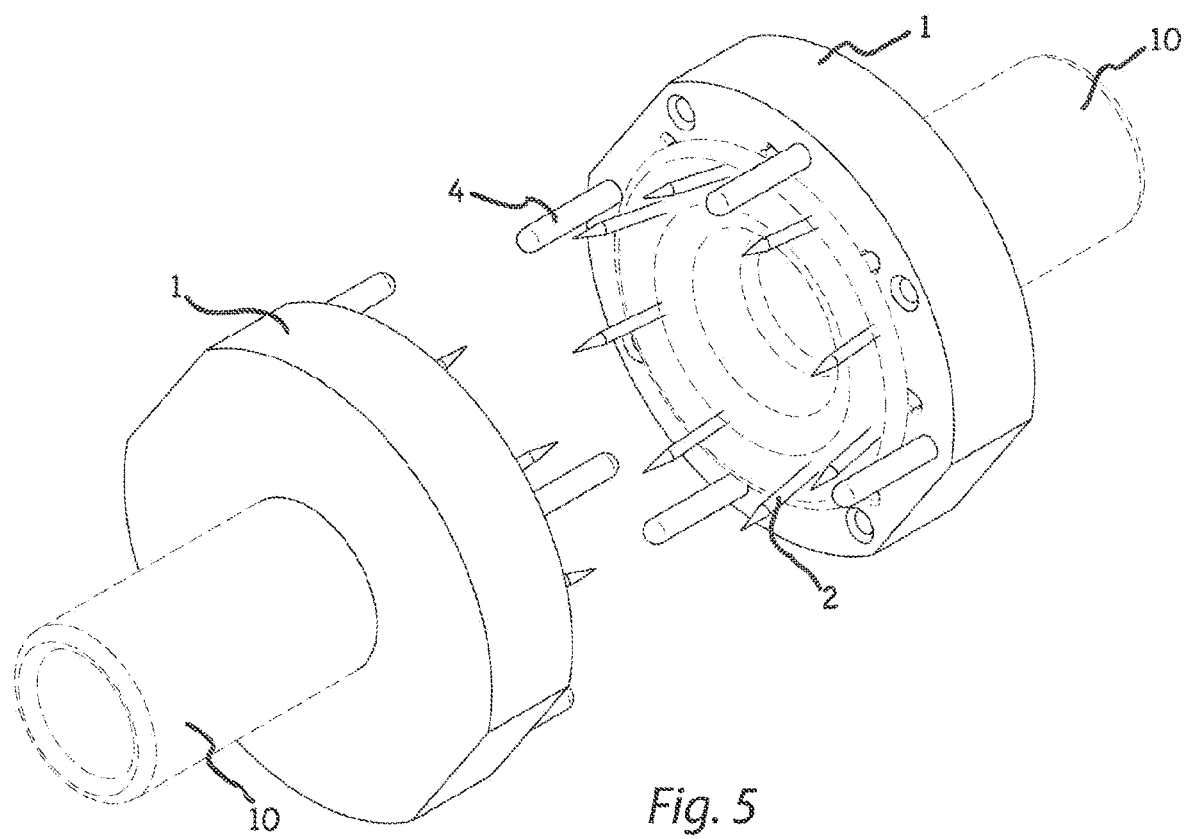
FIG. 5 shows an oblique perspective view of a pair of coupler rings according to an embodiment of the present disclosure with two artery segments attached thereto, before the coupler rings are joined together.
Figure 6:
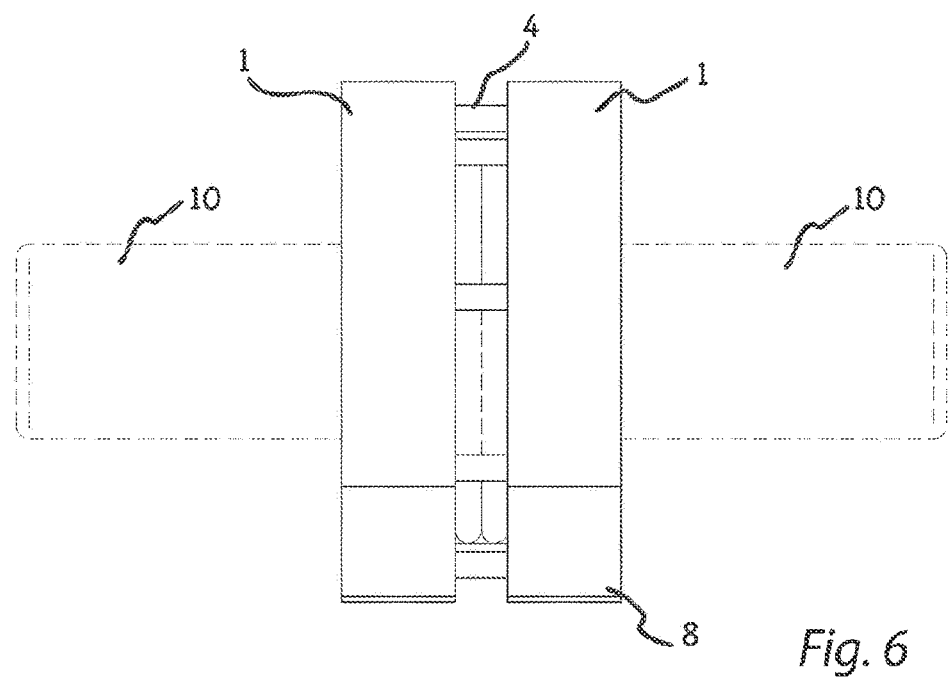
FIG. 6 shows a side view of a pair of coupler rings with two equal-diameter artery segments attached thereto, after the coupler rings are joined together.
Figure 7:
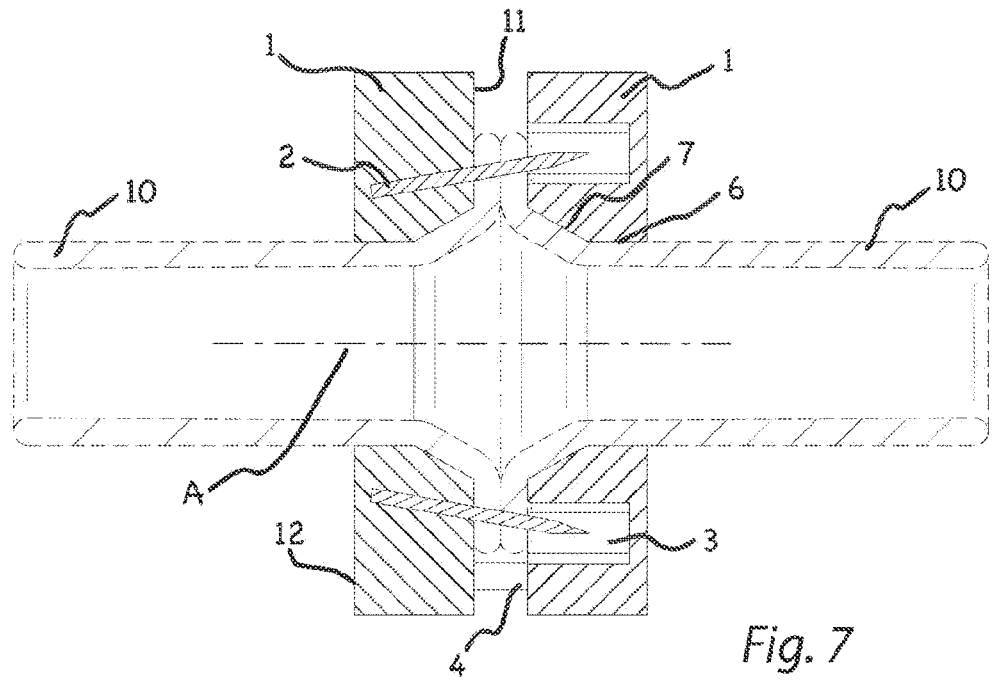
FIG. 7 shows a cross-section view of the assembly of FIG. 6.
Figure 8:
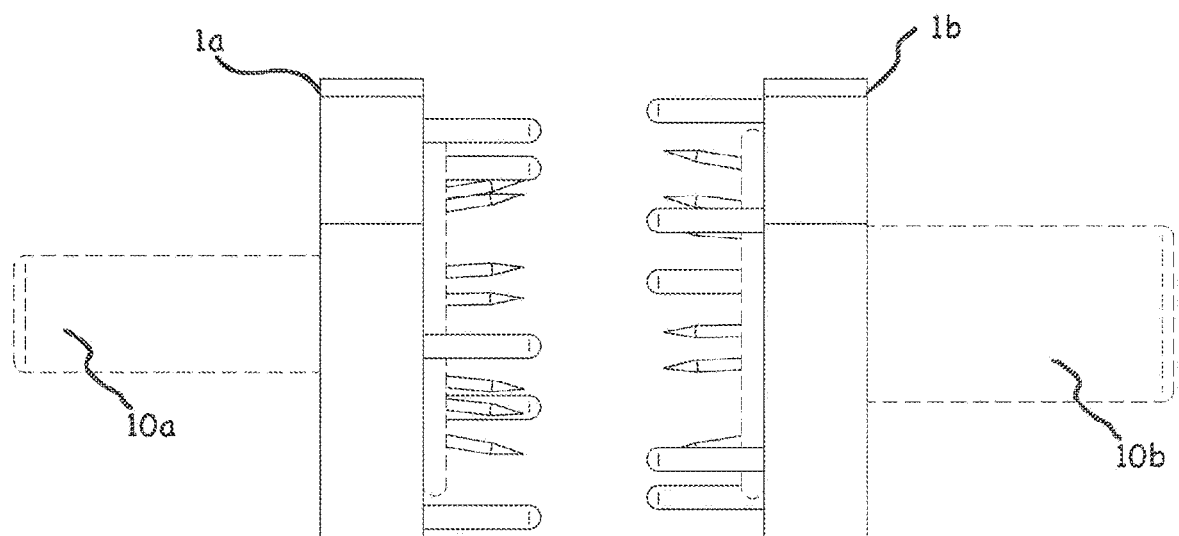
FIG. 8 is an alternative embodiment showing a side view of a pair of coupler rings with two unequal-diameter artery segments attached thereto, before the coupler rings are joined together.

The face 9 of each annulus 1 also includes a plurality of projections or coupler pins 4 extending therefrom. Generally, each annulus 1 has a smaller number of coupler pins 4 than spikes 2, but this may not always be the case. In alternative embodiments, the number of coupler pins 4 may be the same as or more than the number of spikes 2, depending on the particular application. In addition, the diameter and general size of the coupler pins 4 are generally larger than those of the spikes 2, but this may not be true in all embodiments (e.g., the coupler pins may be substantially the same size as the spikes). In the embodiment shown, there are four total coupler pins 4 on each annulus 1, but other embodiments may include annuli with more or less coupler pins. Each coupler pin 4 may be located at a same radial distance from the central axis A of the annulus 1, and may also be spaced equidistantly from one another around the central axis A. For example, the four coupler pins 4 in the illustrated embodiment are spaced apart 90 degrees from one another relative to the central axis A. In general, coupler pins 4 are positioned farther away radially from the central axis A than spikes 2 are from the central axis A. Furthermore, in contrast to the tilted spikes 2, each coupler pin 4 may extend in a direction substantially parallel to the central axis A. The free ends of coupler pins 4 may be rounded or pointed, among other shapes. In some embodiments, coupler pins 4 may also have concentric grooves or protrusions. In addition, similar to the receptacles 3 configured to receive the spikes 2, the face 9 of each annulus 1 further defines a plurality of receptacles or holes 5 having dimensions suitable for accommodating the coupler pins 4 on the opposite annulus 1. As an example, as seen in FIGS. 1-7, the coupler pins 4 and holes 5 can be alternately arranged around the aperture 6, and similar to spikes 2 and receptacles 3, the coupler pins 4 and holes 5 of opposite annuli 1 can be aligned with one another to facilitate movement of the annuli 1 towards one another when opposite coupler pins 4 are received in corresponding holes 5. In addition, similarly to the coupler pins 4, the holes 5 are also constructed to run substantially parallel with the central axis A. That is, the axis of each coupler pin 4 is coaxial with a hole 5 on the opposite annulus 1, to facilitate easy assembly of each coupler pin 4 with an opposite hole 5. In general, there are one or more rotational orientations that can be achieved between opposing annuli 1 of a coupling assembly, where all of the spikes 2 are aligned with opposing receptacles 3 and all of the coupler pins 4 are aligned with opposing holes 5, to facilitate an easy complementary assembly and locking between the opposing annuli 1, for example, as seen in FIGS. 4, 6, and 7. In some embodiments, the holes 5 may be undersized, so as to have a slightly smaller diameter than the diameter of coupler pins 4, in order to facilitate a press-fit connection therebetween. However, other embodiments may facilitate locking between opposite annuli 1 in other manners, in which case the holes 5 may instead have the same or a greater diameter than the coupler pins 4.

As discussed above, a central bore or aperture 6 extends coaxially through the center of each annulus 1 and is open at both the first side 12 and the second side 11. The aperture 6 is generally constructed to be large enough to pass and house an intended end of a tubular structure to be anastomosed. For example, different annuli 1 may have different sized apertures within a range of 1 mm to 5 mm (or larger or smaller in other applications), and may be appropriately selected corresponding to a similarly sized artery. In the embodiment shown, the aperture 6 is generally cylindrical in shape, with a circular cross-section, although in other embodiments, the central aperture may be constructed in any of various different shapes, depending on the anatomical tubular structure intended to be attached thereto. Furthermore, in the embodiment shown, a bevel 7 is formed in at least part of the aperture 6. The bevel 7 in the illustrated embodiment starts approximately halfway through the aperture 6 and widens towards the second side 11, but in other embodiments, different sized and angled bevels may be employed, or no bevel may be included at all. Furthermore, the edges formed between the aperture 6 and the bevel 7, and/or between the aperture 6 and/or the bevel 7 with the respective sides 11, 12 of the annulus 1, may in some cases be rounded, to reduce abrasion with and potential damage to an attached tubular structure.

Figure 2:
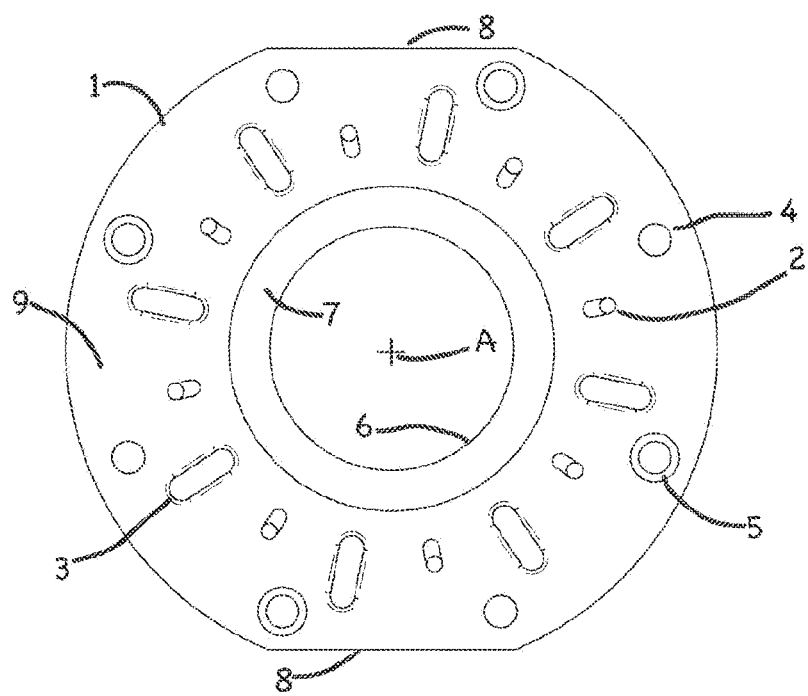
FIG. 2 shows a front view of the one coupler ring of FIG. 1.
Figure 3:
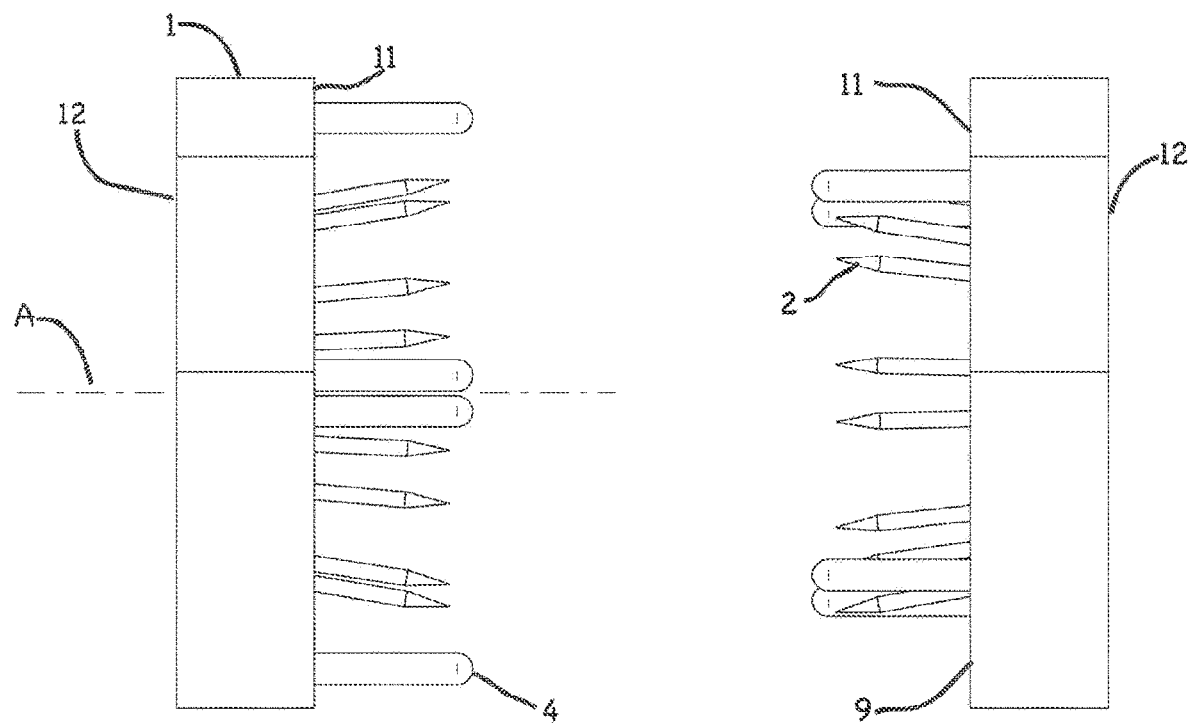
FIG. 3 shows a side view of a pair of coupler rings according to an embodiment of the present disclosure before they are joined together.

In addition, to aid in proper alignment between the respective annuli 1 during assembly, each annulus 1 may further include an alignment feature. For example, as shown in the embodiment of FIGS. 1-7, the outer surface of each annulus 1 may be constructed with one or more flat regions 8 (two in the illustrated example, as best seen in FIGS. 2 and 4). Here, so long as the flat regions 8 of opposing annuli 1 are aligned, then a practitioner can easily confirm that the annuli 1 are rotationally aligned, such that spikes 2 will all properly fit into receptacles 3 and coupler pins 4 will all properly fit into holes 5, during either assembly with a tool or assembly by hand. Other alignment features, such as projections or visual markings, are also contemplated.

In use, for an arterio-arterial anastomosis, two arterial segments are joined end-to-end. One segment of an artery is pulled through the aperture 6 of a first annulus 1 of a coupling assembly. The end of the artery 10 is everted, impaled, and anchored on to spikes 2, as best shown in FIG. 5. The process is repeated with a second annulus 1 of the coupling assembly and a second arterial segment. As best seen in FIG. 7, the bevel 7 formed in the aperture 6 allows the artery wall to make a more gradual transition when it is widened towards the second side 11 of the annulus 1 and anchored onto the spikes 2, and the bevel 7 (and/or any rounded edges between transitions as discussed above) may serve to reduce strain on the artery wall when connected to the annulus 1. Meanwhile, in some situations, even after attachment to an annulus 1, the arterial wall 10 may not initially be fully everted after being pulled over the spikes 2. In these instances, full eversion of the arterial wall 10 and compression against the second side 11 may occur later, after two opposing annuli 1 are mated together, as discussed in greater detail below.

To aid proper alignment, the flat regions 8 are located on the side of each annulus to act as indexing surfaces. When properly aligned, the two annuli 1 will be coaxial and the flat regions 8 will be coplanar as shown in FIGS. 4 and 6, and in this rotational orientation, the spikes 2 of each annulus 1 will be aligned with the receptacles 3 of the opposing annulus 1, and the coupler pins 4 of each annulus will be aligned with the holes 5 of the opposing annulus. When properly aligned, the two annular rings 1 are brought together so that the ends of the two arterial segments are pressed together to form a leak-free anastomosis, for example, as shown in FIG. 6. The two annuli 1 may be held together as an assembly by the tight press fit of coupler pins 4 in holes 5 as discussed above, or may be held together in other mechanical and/or adhesive means in other embodiments. To further ensure the two annuli stay attached, in some embodiments, coupler pins 4 may include concentric grooves or protrusions formed thereon, and holes 5 may contain corresponding protrusions or grooves, to effect, for example, a snap-fit or form-fit connection between the coupler pins 4 and the holes 5. Coupler pins 4 may have rounded or pointed ends to facilitate proper insertion into holes 5. Spikes 2 generally will have sharply pointed ends to easily pierce the artery, to facilitate easy attachment thereto. The diameter of aperture 6 can be selected to correspond to the diameter of the artery. For example, different annuli 1 having differently sized apertures, for example, with diameters ranging from 1 mm to 5 mm in preferred embodiments, may be made available and selected based on the artery or other tubular structure the annulus 1 is intended to be used with. Annuli 1 with larger and/or smaller diameters are also possible in other embodiments. If equal sized artery segments are being joined, then the two annuli 1 that are selected for use can be identical. On the other hand, if differently sized artery segments are being joined, then the two annuli 1 may be different (e.g., the size of the aperture in a first annulus may be larger or smaller than the size of the aperture in a second annulus), discussed in greater detail below. The alignment of spikes 2 in one annulus 1 with receptacles 3, e.g., slots or holes, in the other annulus 1 is accomplished through careful choices of the placement of the receptacles and spikes with respect to the flat regions 8 during design and/or manufacturing. Furthermore, also as discussed above, the flat regions 8 which act as indexing surfaces also act to rotationally align, relative to the axes A of the annuli 1, the coupler pins 4 with the receptacles 5 which are arranged to receive them.

Upon merging of opposing annuli 1 of the coupling assembly according to embodiments of the present disclosure, two ends of opposing tubular structures can be effectively held against and attached with one another without leakage in a successful anastomosis. As can best be seen in the cross-sectional view of FIG. 7, in addition to attaching its own tubular vessel or structure to the respective annulus 1, at least some of the spikes 2 from at least one annulus 1 may further impale the everted region of the tubular vessel or structure connected to the opposite annulus 1, further forcing the two tubular vessels or structures together. Therefore, as the opposing annuli 1 are held closely together when the coupling assembly is locked together, the everted surfaces of the two opposing tubular vessels or structures may not only be pressed together between the faces 9 of the opposing annuli 1, but may also be impaled together on one or more of the spikes 2, further enhancing the connection therebetween.

Another embodiment of the present disclosure is shown in FIGS. 8-12, in which the coupling assembly is configured to accommodate and anastomose ends of arteries or other tubular structures 10*a*, 10*b* that may have different diameters. This can be achieved, for example, by selecting and providing annular bodies 1*a*, 1*b*, that have apertures or passageways 6*a*, 6*b* with different sizes (e.g., diameters D1 and D2) to accommodate the different diameter tubular vessels or structures. In the embodiment shown, while the internal bores or apertures 6*a*, 6*b*, of the annular bodies 1*a*, 1*b* have different internal diameters D1, D2, the annular bodies 1*a*, 1*b*, themselves may have substantially common outer diameters OD measured at outer peripheries 13 of the annular bodies 1*a*, 1*b*, to facilitate the anastomosis of the vessels 10*a*, 10*b* having different diameters with a coupling assembly that has a more uniform or consistent outer profile when coupled or locked together. For example, artery 10*a* could be approximately 2 mm in diameter and artery 10*b* could be approximately 3 mm in diameter, as shown in the illustrated embodiment. However, annular bodies with different sized internal apertures may not necessarily have outer profiles with the same or similar size or shape, and some alternative embodiments may include annular bodies with differently sized or even differently shaped outer profiles.

Typically, the central aperture or passageway 6*a*, 6*b* of each annular body 1*a*, 1*b*, will be constructed similarly to aperture 6 discussed with respect to the first embodiment in FIGS. 1-7. The passageways 6*a*, 6*b* may be cylindrical in shape, and in some embodiments, may further include a beveled or flared portion 7 that widens in a direction from the first side 12 towards the second side 11, also as similarly seen in the first embodiment of FIGS. 1-7, to facilitate a smoother transition to the connection region for the tubular structures at the second side 11 of the annular bodies 1*a*, 1*b*. The cylindrical portions of the passageways 6*a*, 6*b* are usually selected to be slightly larger in diameter than the respective arterial or other tubular vessel or structure to be passed through the passageway 6*a* or 6*b*. However, for some procedures, it may instead be desirable to select one or both annular bodies to have passageways that are much larger in diameter, equal to, or even smaller in diameter than the respective arterial or other tubular vessel or structure to be passed through the passageway, depending on the particular characteristics or needs of the patient and/or particular procedure. Also similarly as discussed above, the flared or beveled portion 7, and rounded transitional edges in some embodiments, may reduce stress and/or occurrence of damage to any tubular structure that is connected to the annular body 1*a*, 1*b*.

Figure 9:
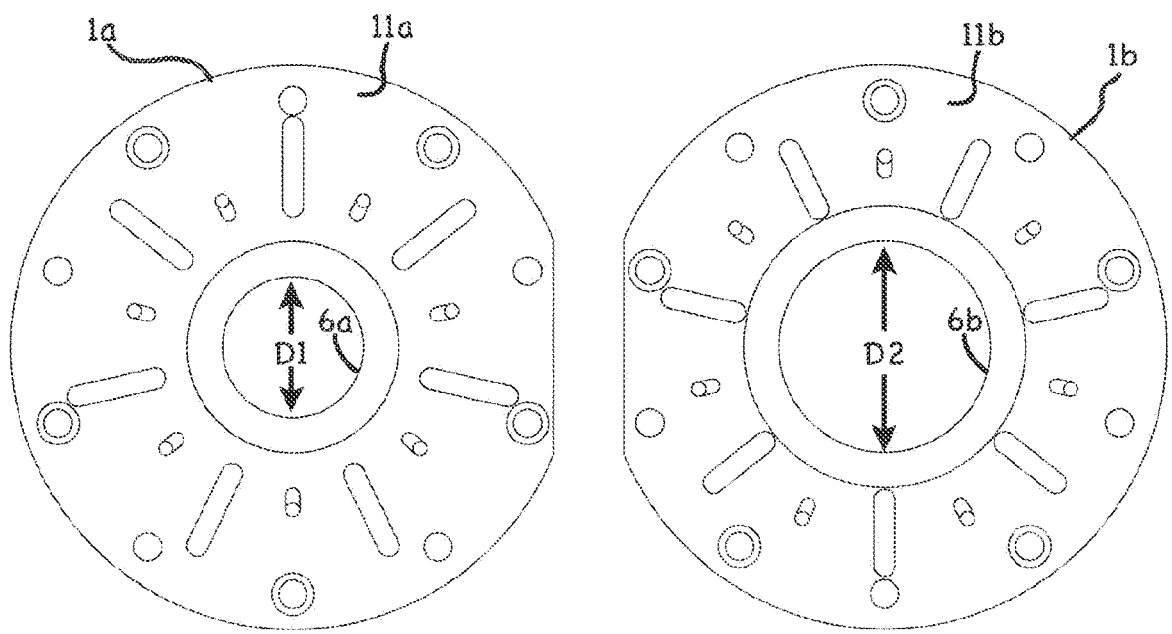
FIG. 9 shows a front view of each coupler ring included in the alternative embodiment shown in FIG. 8, where the coupler rings are different and configured for the two unequal-diameter artery segments.
Figure 10:
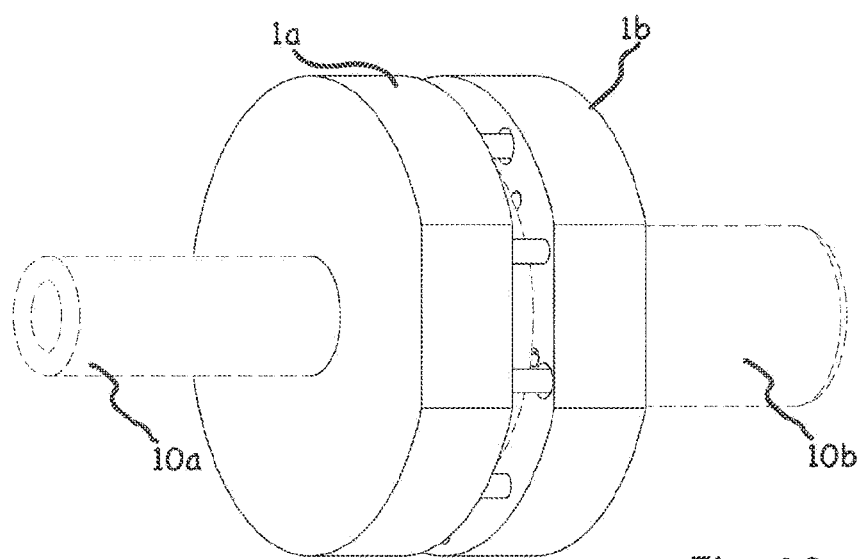
FIG. 10 is an oblique perspective view of the alternative embodiment of the pair of coupler rings with the two unequal-diameter artery segments attached thereto shown in FIGS. 8-9, after the coupler rings are joined together.
Figure 11:
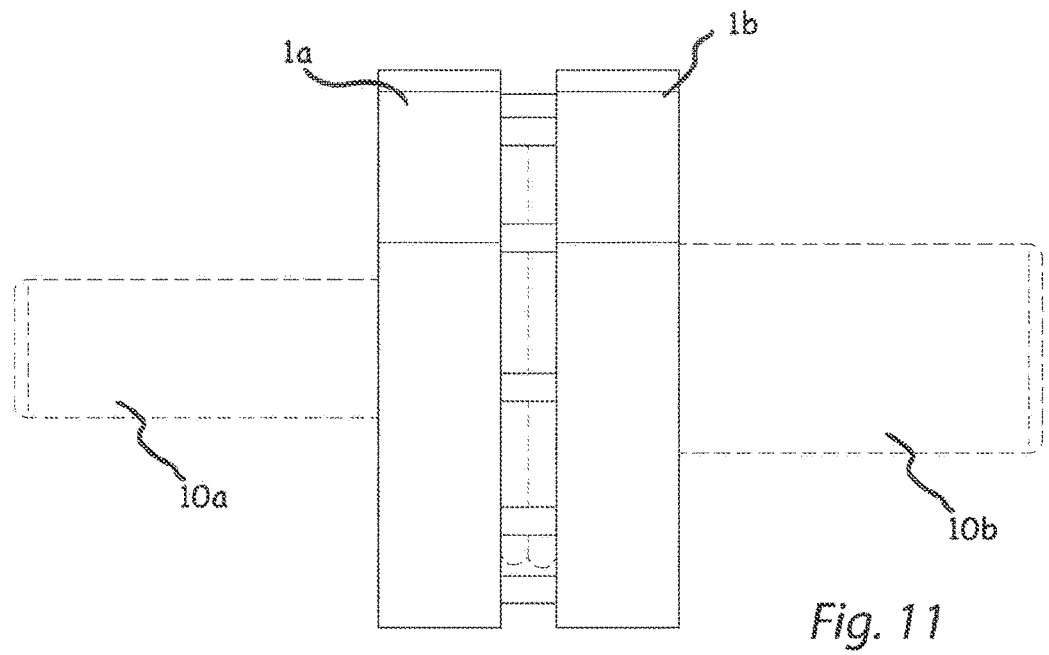
FIG. 11 shows a side view of the assembly of FIG. 10.
Figure 12:
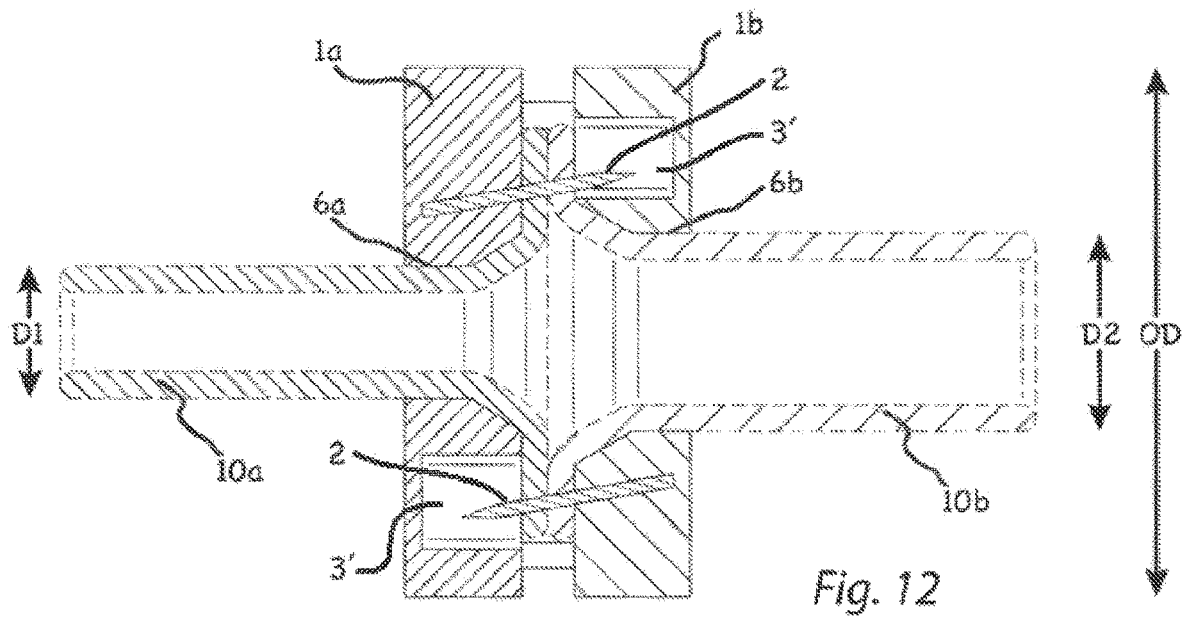
FIG. 12 shows a cross-section view of the assembly of FIGS. 10 and 11.

The spikes 2 and corresponding receptacles 3, as well as the coupler pins 4 and corresponding holes 5, may be similarly arranged on the annuli 1*a*, 1*b*, as they are on the annuli 1 discussed with respect to the first embodiment. Meanwhile, here, a variation is provided where a different number of spikes 2 and receptacles 3 (e.g., seven), as well as a different number of coupler pins 4 and holes 5 (e.g., five) are provided on each of the annuli 1*a*, 1*b*. As discussed above, more or less spikes 2, receptacles 3, coupler pins 4, and/or holes 5 can be arranged on each of the annuli 1*a*, 1*b*, based on the needs of a particular application, so long as the number and positioning of the various complementary features on the opposing annuli 1*a*, 1*b* can be aligned for easy assembly by a practitioner, either with or without assistance from a separate tool. As more clearly shown in FIGS. 8 and 9, the spikes 2 and the receptacles 3 on each of the annular bodies 1*a*, 1*b*, may be alternately arranged and spaced apart equidistantly from one another around the respective central passageways 6*a*, 6*b*. Furthermore, while the passageways 6*a*, 6*b* of the two annular bodies 1*a*, 1*b* have different diameters D1, D2, the spikes 2 of each respective annular body 1*a*, 1*b* may be arranged similarly relative to the respective passageways 6*a*, 6*b*. More specifically, as can best be seen in FIG. 9, the spikes 2 may be spaced apart from the respective passageways 6*a*, 6*b* by substantially a same distance in a radial direction. In other words, regardless of the size of the central passageway 6*a*, 6*b*, the spikes 2 may be positioned, for example, approximately 0.5 mm away from an edge of the passageway 6*a*, 6*b* in a radial direction. More generally speaking, a sufficient or otherwise appropriate radial distance or proximity between the spikes 2 and the passageways 6*a*, 6*b* should be selected such that an attached everted artery will remain attached to the annular body 1*a*, 1*b*, without damaging the artery and/or preventing or reducing detachment of the artery from the annular body 1*a*, 1*b* after attachment. The resulting arrangement is such that, as best seen in FIG. 9, the annular body 1*b*, which has a central passageway 6*b* with a larger diameter D2, has spikes 2 that are positioned farther away in a radial direction from the central axis A and closer to an outer edge 13 of the annular body 1*b*, as compared to the annular body 1*a*, which has a central passageway 6*a* with a smaller diameter D1, and whose spikes 2 are positioned closer to the central axis A and farther away from an outer edge 13 of the annular body 1*a*. As noted above, in alternative embodiments, the different annular bodies may have differently sized or shaped outer profiles, and as such, the distances of the spikes 2 from a corresponding outer edge of a respective annular body may vary from those described with respect to the illustrated embodiment.

Meanwhile, the coupler pins 4 and the holes 5 located on each of the annular bodies 1*a*, 1*b*, are spaced apart from the central axes A of their respective annular bodies 1*a*, 1*b*, at common radial distances, such that they can be aligned with and easily engage their respective complementary features on the opposing annular bodies 1*b*, 1*a*, in order to facilitate the annular bodies 1*a*, 1*b* coupling with one another in an assembled state to anastomose everted vessels having different diameters.

Both annular bodies 1*a*, 1*b* include spike-receiving receptacles 3'. In the embodiments shown, the receptacles 3' are substantially similarly arranged. In other words, the receptacles 3' each have substantially the same shape and are oriented substantially the same as one another in the radial direction. In some embodiments, the receptacles 3' may also be substantially similarly sized between annular bodies (i.e., the receptacles 3' may each have substantially the same radial length, regardless of the size of the passageways and/or spikes of the respective annular body), but this may not always be the case, depending on space constraints caused by larger passageways that take up more space on a respective annular body. Furthermore, the receptacles 3' of the annular bodies 1*a*, 1*b* are spaced apart from the respective central axis A by substantially the same distance. In other words, the positioning and orientation of the receptacles 3' is consistent and substantially similar between the annular bodies 1*a*, 1*b*, even though the spikes 2 of the two annular bodies 1*a*, 1*b* may not be in axially opposite relation to one another when the axes of both annular bodies are coaxial in the coupled condition. In general, most importantly, the receptacles 3' are positioned and sufficiently sized in the radial direction to receive the spikes of the opposite annular body when the annular bodies are assembled together, regardless of the positioning of the spikes on the opposite annular body, without deflecting the spikes. That is, the receptacles 3' in these embodiments are generally longer radially than the receptacles 3 in the embodiment of FIGS. 1-7, such that the receptacles 3' are elongate enough in the radial direction to comfortably receive either the spikes 2 on the annular body 1a that are positioned closer to the central axis A or the spikes 2 on the annular body 1b that are positioned farther away from the central axis A. This feature is schematically illustrated in the contrasting cross-sections shown in FIG. 12. In alternative embodiments, the receptacles on a particular annular body may only be sized and positioned to receive spikes from an opposing annular body that has a specific differently sized passageway (e.g., receptacles on an annular body with a 3 mm passageway may only be configured to accommodate spikes on an annular body with a 2 mm passageway, etc.). As can further be seen in the cross-section of FIG. 12, in the described embodiment, the receptacles 3' on annular body 1b are slightly shorter in length than the receptacles 3' on annular body 1a, due to the larger size of passageway 6b. However, the receptacles 3' on annular body 1b are still sufficiently sized to comfortably receive or otherwise accommodate the spikes 2 from the opposing annular body 1a, even though the spikes 2 on annular body 1a are positioned closer to central axis A than the spikes 2 are on annular body 1b.

Also similarly as discussed above with respect to the first embodiment in FIGS. 1-7, each of the annular bodies 1a, 1b, may further include one or more flat regions 8 that act as indexing surfaces that facilitate easier rotational alignment between the annular bodies 1a, 1b, relative to the axes A of the respective annular bodies. Meanwhile, as most clearly contrasted between FIG. 2 and FIG. 9, some embodiments, for example the one shown in FIGS. 1-7, may be rotationally symmetric to a particular order, for example an order of 4, such that the pattern of spikes, receptacles, pins, and holes are repeated every 90 degrees. Here, if two indexing surfaces 8 are provided as shown, then the annular bodies can be successfully assembled together by aligning the indexing surfaces, even if one annular body is rotated by 180 degrees. Meanwhile, if four indexing surfaces are provided in another embodiment, then those annular bodies can be successfully assembled together with the indexing surfaces at any 90 degree interval. In contrast, in the embodiment shown in FIGS. 8-12 and in some other embodiments, there may be no repeating rotational segments, such that there is only a single proper rotational alignment between two respective annular bodies 1a, 1b. In such cases, only one indexing surface may be provided instead, to prevent inadvertent misalignment. Other alignment features, such as projections or visual markings, may be used instead of or in addition to the one or more flat regions 8.

Even though the annular bodies 1a, 1b differ with respect to the diameters of the passageways 6a and 6b, the respective spikes 2 on the annular bodies 1a, 1b may in some embodiments be inclined at substantially common or similar angles (e.g., 10 degrees, similarly as discussed above) relative to the axis A of the respective annular body 1a, 1b on which the spike is located. In alternative embodiments, the angulation of the spikes 2 may be different on annular bodies with different sized central passageways, depending on the particular application and/or properties of the tubular vessels or structures to be anastomosed. Furthermore, in some embodiments, one or both of the respective passageways 6a, 6b of the annular bodies 1a, 1b, may include a previously described flared or beveled region 7. In some embodiments, the inner passageways or peripheral surfaces of the annular bodies 1a, 1b may diverge similarly, with the beveled regions 7 widening at substantially the same angle relative to the axis A of the respective annular body 1a, 1b, irrespective of the diameter of the corresponding passageway 6a, 6b. In alternative embodiments, the angles of the flared regions 7 may be different for annular rings with differently sized central passageways, and/or some central passageways may not include a flared region 7 at all. Thus these features, among others, may in some embodiments remain the same without affecting the performance of the annular rings or coupler rings, despite use of the rings for vessels with different diameters, so as to reduce the number of differences between coupler rings that can be used together with one another, and thereby add modularity and minimize manufacturing costs for the embodiment shown in FIGS. 8-12.

Generally speaking, similarly as discussed above, when comparing the first embodiment of FIGS. 1-7 and the second embodiment of FIGS. 8-12, the receptacles 3' of the second embodiments are generally sized larger in the radial direction than the receptacles 3 of the first embodiment. In contrast, in both embodiments, each of the tilt angles of the spikes 2 and the angles of the flared portion 7 of the inner peripheral wall that defines the aperture or passageway 6 relative to the central axis A of the respective annular body may in some variations be substantially the same. In addition, the coupler pins 4 and the holes 5 may be arranged similarly, so as to facilitate a secure connection between opposing annular rings when the coupling assemblies are assembled and locked together.

A particular usefulness of embodiments of the coupling assembly described herein is that both arteries and veins require connection or anastomosis, for example, in Plastic Surgery and Microsurgery, when transferring tissue from one part of the body to another in the form of "free flap surgery", also known as "free tissue transfer". This surgery is used on a daily basis for the reconstruction of traumatic, congenital, and/or oncologic defects. Embodiments of the coupling assembly may also be utilized in other surgical specialties, for example, for vascular bypass surgery in peripheral vascular disease and in organ transplantation. A main usefulness of embodiments of the present disclosure will be to significantly improve the speed, efficiency, and reliability of arterio-arterial anastomosis, similar to what the venous coupler has done for venous anastomosis. For reference, a single hand sewn anastomosis for arteries can take anywhere from 15-30 minutes, and has a significant error rate, which would require a revision or redo, that could easily double the procedure time. In contrast, an arterio-arterial anastomosis using coupling assemblies according to embodiments of the present disclosure could reduce the anastomosis procedure time by tenfold or more.

Thus, various embodiments of the present disclosure may feature, for example, a flared central passageway through which a tubular vessel or structure can be passed. In this manner, a bevel formed at the inner circumference of the coupler ring may provide a gradual inclined transition from the passageway to a planar face at a second side of the coupler ring which is intended to receive and hold the tubular vessel or structure in an everted condition, instead of a sharp transition of 90 degrees from the surface defining the passageway to the surface at the second side. Further, various embodiments of the present disclosure may include a ring-shaped array of angled spikes, so that arterial or other vessel wall eversion is obtuse and therefore will not disrupt integrity of the arterial or other vessel wall, as compared to spikes oriented substantially perpendicularly to the planar face of the second side of the coupler ring that is arranged to receive the everted vessel. The various embodiments of the present disclosure may also incorporate integration of different internal diameter coupler rings to be used together, such that arterial vessel diameter discrepancies can be accommodated. The two mating rings of the coupler assembly may not always be identical.

It will be appreciated that the unique functionality of the coupling apparatus according to embodiments of the present disclosure is provided by, for example, the tilted spikes, the receptacles which receive the spikes, and/or the beveled edge formed in the central aperture or passageway. In the embodiments illustrated herein, a first set of spikes can be used to hold the blood vessel or other tubular structure to the coupler rings, and another independent set of coupler pins can be used to hold the coupler rings together upon final assembly or locking. The first set of spikes may be tilted to hold the artery or other tubular structure in place relative to the attached coupler ring. Arteries, for example, are generally more stiff than veins, and will therefore tend to pop off or detach from coupler rings with perpendicularly arranged spikes.

A separate tool (or tools) can be used to hold two coupler rings in place and to press the two coupler rings together to form a final coupling assembly where the attached tubular vessels or structures are anastomosed. Similar such tools are well known in the art, as evidenced for example in U.S. Pat. Nos. 8,313,013, 4,607,637, 4,624,257, 4,917,090, or U.S. Pat. No. 4,917,091, and thus, a tool for use with embodiments of the present disclosure will not be described in further detail herein.

In summary, as described herein, various embodiments of the coupling apparatus for anastomosis of tubular vessels or other tubular structures may generally include two or more annuli with one or more of the following features: a relatively thin and flat profile, a beveled central aperture, a plurality of spikes tilted away from a central axis of each annulus and/or pointed at their free ends to facilitate impaling of an end of an artery or other tubular structure, a plurality of receptacles, e.g., slots or holes, that alternate with said spikes, each receptacle being configured to accommodate a spike from an opposite annulus, a plurality of coupler pins that may extend parallel to the central axis of the annulus, a plurality of holes that are distinct from the receptacles for the spikes to accommodate the coupler pins, concentric grooves or protrusions formed on the coupler pins and/or corresponding protrusions or grooves formed in the holes, and/or flat sides formed on an outer surface of each annulus to properly rotationally align two opposing annuli of a coupling assembly. Various other modifications may further be contemplated without departing from the spirit and/or scope of the present invention.

The scope of the claims should not be limited by the preferred embodiments set forth in the examples but should be given the broadest interpretation consistent with the specification as a whole.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An apparatus for anastomosis of tubular structures comprising two implantable annular bodies, each of the annular bodies comprising:
   a first side;
   a second side, wherein a central axis extends between the first and second sides;
   an inner wall defining a passageway for passing a tubular structure therethrough, wherein the passageway extends along the central axis and is open to the first and second sides;
   a plurality of spikes each comprising a base and a pointed free end configured to pierce the tubular structure; and
   a plurality of receptacles formed into the second side of the annular body, each of the receptacles being elongate in shape with an axis of extension of the elongate shape extending radially relative to the central axis;
   wherein when the annular bodies are assembled together, at least part of one of the annular bodies extends past the second side of the other annular body and engages the other annular body to hold the annular bodies together, the second sides of each of the annular bodies face one another, the central axes of the annular bodies are coaxial, respective bases of each of the spikes of the annular bodies extend from the second side of the annular body towards the opposing annular body with longitudinal axes that are angled relative to the central axis when the spikes are unbiased such that for each of the spikes, the free end is positioned farther from the central axis in a radial direction than the base is to the central axis, and each of the receptacles is configured to receive a corresponding one of the plurality of spikes of the opposing annular body when the annular bodies are assembled together.

2. The apparatus of claim 1, wherein the plurality of spikes are located at a same radial distance from the central axis as one another.

3. The apparatus of claim 1, wherein the plurality of spikes are spaced equidistantly from one another in a circumferential direction around the passageway.

4. The apparatus of claim 1, wherein each of the spikes is angled along a radial direction relative to the central axis.

5. The apparatus of claim 1, wherein each of the receptacles has two closed ends along the axis of extension of the elongate shape of the receptacle.

6. The apparatus of claim 1, wherein the plurality of spikes and the plurality of receptacles are alternately arranged around the passageway on the second side.

7. The apparatus of claim 1, further comprising an alignment feature on each annular body to facilitate proper alignment of the respective spikes and receptacles of the annular bodies when the annular bodies are assembled together.

8. The apparatus of claim 1, wherein the passageway of a first one of the annular bodies is wider than the passageway of a second one of the annular bodies for anastomosing respective tubular structures that have different sizes.

9. The apparatus of claim 8, wherein a radial distance between each of the plurality of spikes and the passageway of the first annular body is substantially the same as a radial distance between each of the plurality of spikes and the passageway of the second annular body, such that the plurality of spikes on the first annular body are located at a greater radial distance from the central axis of the first annular body than the plurality of spikes on the second annular body are from the central axis of the second annular body.

10. The apparatus of claim 1, wherein the longitudinal axes of the bases of each of the spikes of the annular bodies remains angled relative to the central axis prior to assembling the annular bodies together.

11. The apparatus of claim 1, wherein at least one of the spikes of the one of the annular bodies extends past the second side of the other annular body into the other annular body.

12. The apparatus of claim 1, wherein when the annular bodies are assembled and held together, the free ends of each of the spikes remains pointed axially away from the first side of the annular body to which the spike is connected.

13. The apparatus of claim 1, wherein when the annular bodies are assembled and held together, each of the spikes remains straight without any bends.

14. The apparatus of claim 1, wherein the at least part of the one of the annular bodies that is configured to extend past the second side of the other annular body to engage the other annular body and to hold the annular bodies together is sized and/or shaped differently from at least one of the spikes.

15. An apparatus for anastomosis of tubular structures comprising two implantable annular bodies, each of the annular bodies comprising:
a first side;
a second side, wherein a central axis extends between the first and second sides, and wherein the second sides of the annular bodies face one another and the central axes of the annular bodies are coaxial when the annular bodies are assembled together;
an inner wall defining a passageway for passing a tubular structure therethrough, wherein the passageway extends along the central axis, has a first opening at the first side, a second opening that is wider than the first opening at the second side, and a transition region between the first and second openings, wherein in a cross-section including the central axis of the annular body, the transition region comprises a flat tapered wall whose inner width increases as the transition region extends towards the second opening; and
a plurality of spikes extending from the second side, each spike comprising a pointed free end for piercing the tubular structure.

16. The apparatus of claim 15, wherein the passageway has a first portion adjacent to the second side of the annular body that widens as the passageway extends in a direction from the first side towards the second side.

17. The apparatus of claim 16, wherein the passageway further has a second portion adjacent to the first side of the annular body that has a substantially cylindrical profile.

18. The apparatus of claim 15, wherein the plurality of spikes each extends from an end face at the second side of the annular body to which it is connected.

* * * * *